(12) United States Patent
Vertoprakhov et al.

(10) Patent No.: US 9,140,545 B2
(45) Date of Patent: Sep. 22, 2015

(54) OBJECT INSPECTION SYSTEM

(75) Inventors: Victor Vertoprakhov, Novosibirsk (RU); Tian Poh Yew, Singapore (SG)

(73) Assignee: VISIONXTREME PTE LTD, Singapore (SG)

( * ) Notice: Subject to any disclaimer, the term of this patent is extended or adjusted under 35 U.S.C. 154(b) by 642 days.

(21) Appl. No.: 12/711,270

(22) Filed: Feb. 24, 2010

(65) Prior Publication Data

US 2010/0220185 A1    Sep. 2, 2010

(30) Foreign Application Priority Data

Feb. 24, 2009 (SG) .................................. 200901303

(51) Int. Cl.
| | | |
|---|---|---|
| *H04N 7/18* | (2006.01) | |
| *G01B 9/00* | (2006.01) | |
| *G06K 9/00* | (2006.01) | |
| *G01B 11/24* | (2006.01) | |
| *G01M 11/02* | (2006.01) | |
| *G01N 21/958* | (2006.01) | |
| *G01N 21/88* | (2006.01) | |

(52) U.S. Cl.
CPC ............ *G01B 11/24* (2013.01); *G01M 11/0278* (2013.01); *G01N 21/958* (2013.01); *G01N 2021/8867* (2013.01)

(58) Field of Classification Search
CPC .................. G01N 21/8806; G06T 2207/30164; G06T 7/0004; G06T 7/001; H04N 7/183
USPC ........ 348/92, 369; 345/166; 351/206; 355/53; 382/148, 149, 141

IPC ...... G06K 9/62,9/00; G09G 5/08; H04N 5/238, H04N 5/262, 7/18; G01B 9/00
See application file for complete search history.

(56) References Cited

U.S. PATENT DOCUMENTS

| | | | | |
|---|---|---|---|---|
| 4,589,140 | A * | 5/1986 | Bishop et al. ................. | 382/148 |
| 5,610,710 | A * | 3/1997 | Canfield et al. ............ | 356/237.6 |
| 6,072,899 | A * | 6/2000 | Irie et al. ...................... | 382/149 |
| 6,717,142 | B2 * | 4/2004 | Hiroi et al. ...................... | 850/5 |
| 6,928,185 | B2 * | 8/2005 | Yonezawa .................... | 382/149 |
| 2003/0215127 | A1 * | 11/2003 | Stern et al. .................... | 382/141 |
| 2007/0008286 | A1 * | 1/2007 | Theytaz et al. ............... | 345/166 |
| 2008/0088795 | A1 * | 4/2008 | Goldstein et al. ............ | 351/206 |
| 2008/0239267 | A1 * | 10/2008 | Suzuki et al. .................. | 355/53 |
| 2009/0060315 | A1 * | 3/2009 | Harris et al. .................. | 382/141 |
| 2009/0167933 | A1 * | 7/2009 | Miura et al. .................. | 348/369 |

* cited by examiner

*Primary Examiner* — Thao X Le
*Assistant Examiner* — Long Le
(74) *Attorney, Agent, or Firm* — Axis Intellectual Capital Pte Ltd; Leif A. Sloan; Sonya C. Harris

(57) ABSTRACT

Early techniques for object inspection relied on human inspectors to visually examine objects for defects. However, automated object inspection techniques were subsequently developed due to the labor intensive and subjective nature of human operated inspections. Additionally, object characteristics such as object power and object thickness need to be determined after the objects have been examined for defects. Conventionally, corresponding inspection stations are along the manufacturing lines for determining each of the object characteristics. However, the need for human intervention and time spent to move the objects from one inspection station to another adversely affect the efficiency of the object manufacturing process. An embodiment of the invention disclosed describes a high-resolution object inspection system for performing object inspection.

26 Claims, 7 Drawing Sheets

OBJECT INSPECTION SYSTEM

FIELD OF INVENTION

The present invention relates generally to systems for inspection of objects. More specifically, the present invention relates to a optical media or lens inspection system.

BACKGROUND

Early techniques for inspecting lenses typically relied on human inspectors to visually examine the lenses for defects (hereinafter referred to as lens defects) usually by placing the lenses under magnification or projection onto a screen whereupon the human inspectors then visually search for lens defects. However, the labour intensive and subjective nature of human operated inspections prompted interest in automating the inspection process. Numerous methods have been investigated, foremost of which are those whereby an image of a lens is acquired and the image then being electronically evaluated for lens defects. Commonly, these methods take advantage of the fact that light, under certain circumstances when encountering a lens irregularity, scatters in a manner that can be qualitatively assessed. These methods generally operate by manipulating a light beam before and/or after passing through a lens in order to extract optical information that is subsequently analysed to assess for flaws.

U.S. Pat. No. 5,500,732 to Ebel et at al and U.S. Pat. No. 6,134,342 to Doke et at describe a conventional system and method for lens inspection. The conventional system and method as described by Ebel and Doke transport lenses using a holder, such as a curvette. However, the conventional system and method is only suited for inspecting lenses that are dry and cannot be applied to inspect ophthalmic or contact lenses that are transported in a medium such as saline solution. Most contact lenses in the market are packaged in saline solution. This causes technical challenges for obtaining high definition images of contact lenses in saline solution for inspection thereof.

As demands for detecting defects of smaller dimension increases, it is necessary to use images of higher resolution to detect such defects. U.S. Pat. No. 6,301,005 to Epstein et al describes a conventional system and method for high resolution lens inspection. However, such high resolution lens inspection requires cameras that are costly and subject to availability. It is therefore difficult to obtain high definition images of the lenses without the use of the foregoing cameras.

Additionally, lens characteristics such as lens power and lens thickness are typically determined after the lenses have been examined for defects. Conventionally, inspection stations are along the lens manufacturing lines in which each inspection station independently measures and determines the corresponding lens characteristics. However, the time spent to transfer the lenses from one inspection station to another adversely affects the efficiency of the lens manufacturing process and hence lowers the overall yield of lens production. Moreover, the need for human intervention during the transferring of lenses from one inspection station to another potentially creates opportunities for human-related mistakes to occur.

Accordingly, there exists a need for a system for addressing the foregoing problems of existing lens inspection systems by minimizing the need to physically transfer the lenses between inspection stations thereby improving the overall efficiency for lens manufacturing.

SUMMARY

The present embodiments of the invention disclosed herein provide a high-resolution object inspection system for performing object inspection.

In accordance with a first aspect of the invention, there is disclosed an object inspection system for inspecting an object, comprising a first station, a second station and a third station. The first station captures a first image of the object in which the first image is processable to determine one of presence and absence of at least one defect on the object. The second station captures at least one second image in which the at least one second image is a magnified view of at least one portion of the object. The at least one second image is processable to determine quality of the at least one defect and the quality of the at least one defect is one of acceptable and unacceptable. The third station determines optical property such as the object power and thickness of the object upon one of absence of the at least one defect and the quality of the at least one defect being determined as acceptable from the at least one second image.

In accordance with a second aspect of the invention, there is disclosed an object inspection method comprising capturing a first image of an object by a first station. The first image is processable to determine one of presence and absence of at least one defect on the object. The method also comprises capturing at least one second image by a second station in which the at least one second image is a magnified view of at least one portion of the object. The at least one second image is processable to determine quality of the at least one defect and the quality of the at least one defect is one of acceptable and unacceptable. Lastly, the method comprises determining optical property such as the object power and thickness of the object by a third station upon one of absence of the at least one defect and the quality of the at least one defect being determined as acceptable from the at least one second image.

BRIEF DESCRIPTION OF THE DRAWINGS

Embodiments of the invention are disclosed hereinafter with reference to the drawings, in which.

DETAILED DESCRIPTION

Figure 1:
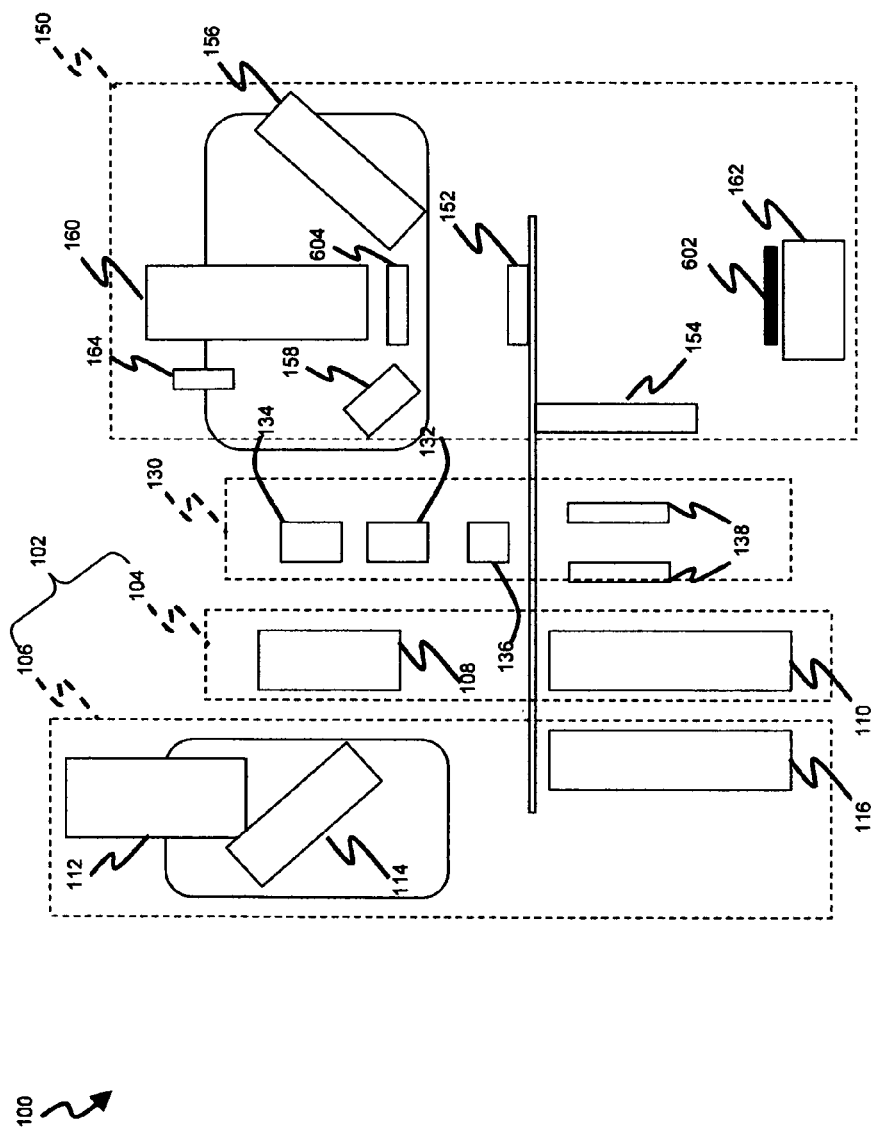
FIG. 1 shows a high-resolution lens inspection system according to an embodiment of the invention.

A high-resolution lens inspection system for performing object inspection is described hereinafter for addressing the foregoing problems.

For purposes of brevity and clarity, the description of the invention is limited hereinafter to lens inspection, for instance, involving a lens having at least one of a convex side and a concave side (e.g., a lens corresponding or generally corresponding to a portion of a sphere). This however does not preclude various embodiments of the invention from other applications of similar nature or from applications in inspection of other types of objects. The fundamental inventive principles of the embodiments of the invention are common throughout the various embodiments.

Exemplary embodiments of the invention described hereinafter are in accordance with FIGS. 1 to 7 of the drawings, in which like elements are numbered with like reference numerals.

FIG. 1 shows a high-resolution object inspection system 100 according to an embodiment of the invention. The high-resolution object inspection system 100 is suitable for inspecting objects such as lens, for instance, lens having a convex side and a concave side (e.g., a lens corresponding or generally corresponding to a portion of a sphere) or other manufactured products for detecting defects on the objects. The following description of the embodiments of the invention applies but is not limited to inspection of lenses.

The high-resolution object inspection system 100 comprises three subsystems: a lens defect inspection subsystem 102, a lens placement subsystem 130 and a lens characteristic measurement subsystem 150. The lens defect inspection subsystem 102 serves to assess and detect defects on lenses, such as aberration defects. The lens defect inspection subsystem 102 comprises two inspection stations: a Full Field-of-View (FOV) station 104 and a Magnified Field-of-View (FOV) station 106.

At the Full FOV station 104, an image of a lens is captured and electronically evaluated to detect any defects on the lens. Thereafter, regardless whether defects are detected by the Full FOV station 104, high-resolution images of different portions of the lens are captured using the Magnified FOV station 106 for further inspection of the lens. The multiple high-resolution images of the lens are preferably captured using a device that comprises two mirror galvanometers for focusing different portions of the lens for allowing the high-resolution images to be captured. The mirror galvanometers are preferably variable speed mirror galvanometers. If no defects are detected, the lens is then transferred to the lens placement subsystem 130. However, if defects have been detected, the severity and complexity of the defects determine whether the lens should be accepted or discarded. If the lens is accepted, the lens will be transferred to the lens placement subsystem 130.

Preferably, the object inspection system 100 determines the severity and complexity of detected defects. Alternatively, a human inspector may be alerted to inspect the lens if the high-resolution object inspection system 100 is unable to make a judgement on whether to discard or accept the lens. The Full FOV station 104 comprises a first detection means 108 and a first illumination source 110. Separately, the Magnified FOV station 106 comprises a second detection means 112, a mirror galvanometer 114 and a second illumination source 116. The first and second illumination sources 110/116 are, for example, laser beam emitting sources.

The lens placement subsystem 130 serves to transfer the lens from the lens defect inspection subsystem 102 to the lens characteristic determination subsystem 150. As shown in FIG. 1, the lens placement subsystem 130 comprises a bottom pickup unit 132, a top pickup unit 134, a curvette 136 and actuator motors 138 and operates in association with a lens holder 152. Both the curvette 136 and the lens holder 152 can be positioned relative to a common axis controlled by actuator motor(s) 154. The bottom pickup unit 132 picks up the lens and flips or rotates (e.g., by 180°) and/or inverts the lens. This action results in the lens facing the top pickup unit 134 (for example, the lens becomes inverted or turned "inside out"). The bottom pickup unit 132 then transfers the lens to the top pickup unit 134 and moves away to allow the top pickup unit 134 to place the lens in the curvette 136. The lens holder 152 then moves to the lens characteristic determination subsystem 150 (e.g., without rotation or inversion thereto). Additionally, the actuator motors 138 displace and position the bottom pickup unit 132 and top pickup unit 134 along a plane parallel to the optical axis of the lens.

At the lens characteristic determination subsystem 150, the lens power and thickness of the lens are determined. Lens power essentially measures the focal length of a lens. The lens is first transferred from the curvette 136 onto a lens holder 152. The lens holder 152 is operated by an actuator motor 154 and is movable perpendicular to the optical axis of the lens. The measurement of the lens thickness is performed using a third detection means 156 and a third illumination source 158. Independently, the measurement of the lens power is performed using a fourth detection means 160, a test target 602 and a fourth illumination means 162. The fourth detection means 160 is movable along a plane parallel to the optical axis of the lens and is driven by an actuator motor 164.

Additionally, the first illumination source 110, second illumination source 116 and fourth illumination means 162 provide backlighting to illuminate the lens at the respective subsystems of the high-resolution object inspection system 100. Further, the first illumination source 110, second illumination source 116 and fourth illumination means 162 are preferably operable for varying the amount of illumination to thereby enable images of the lens to be selectively captured and inspected (e.g., under different lighting conditions). The first illumination source 110, second illumination source 116 are preferably operable to emit light along an optical path that includes the lens and the detection means 108, 112. The first detection means 108, second detection means 112, third detection means 156 and fourth detection means 160 are preferably one of complementary metal-oxide semiconductor (CMOS) sensor and a charge-coupled device (CCD) to provide lens imaging. Typically, digital cameras equipped with either the CMOS sensor or the CCD are used in the detection means. The first detection means 108, second detection means 112, third detection means 156 can include imaging elements in a manner understood by one of ordinary skill in the art.

Figure 2:
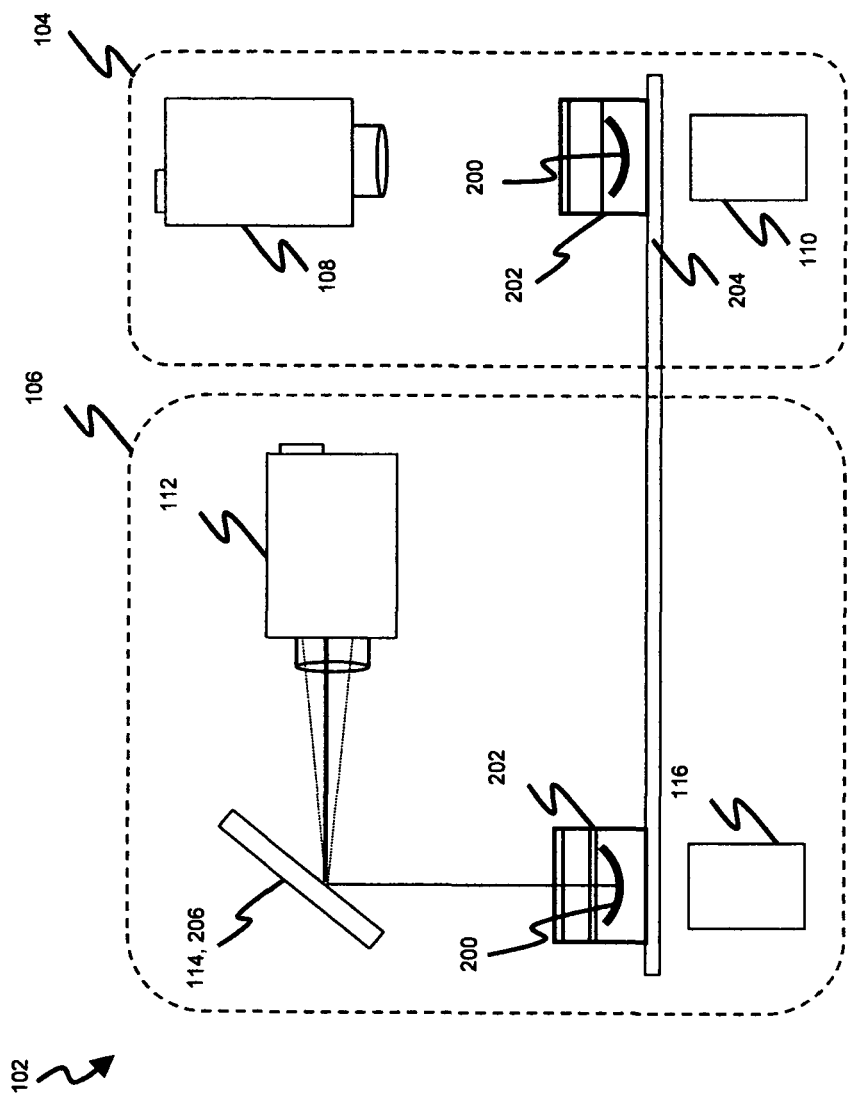
FIG. 2 shows a lens defect inspection subsystem of the high-resolution lens inspection system of FIG. 1 in which the lens defect inspection subsystem comprises a Full Field-of-View (FOV) station and a Magnified Field-of-View (FOV) station.

Details with respect to the Full FOV station 104 and the Magnified FOV station 106 are as shown in FIG. 2. The setup at the Full FOV station 104 shows a lens 200 enclosed in a protective casing or holder 202 that is positioned on a support 204. The holder 202 can carry a lens having a convex and/or concave portion in a manner that facilitates image capture, processing, evaluation, magnification and/or assessment. Illumination is provided by the first illumination source 110 to enable the first detection means 108 to capture a clear image of the lens 200. The image is then digitally processed and evaluated for detecting defects on the lens. If defects are detected, the lens 200 is transferred to the Magnified FOV station 106 for further assessment in which portions of the lens 200 containing the defects are magnified by the second detection means 112. The magnification is performed preferably by taking high-resolution images of the required portions of the lens 200.

In addition, the Full FOV station 104 might not be able to detect very fine defects on the lens. Under such conditions, it is still necessary for the lens to undergo inspection at the Magnified FOV station 106 to ensure that the lens is defect-free. Hence, there are situations in which the defects are only detectable by the Magnified FOV station 106 and not by the Full FOV station 104.

To selectively capture images of any portion of the lens or object 200, usage of the mirror galvanometer 114 or a positionable or steerable mirror 206 in conjunction with the second detection means 112 is required. The mirror galvanometer 114 or positionable or steerable mirror 206 is operable for bringing a portion of the light passing through the object 200 into focus to thereby facilitate capturing images thereof. The detection means 112 captures the images of portions of the lens 200 and thereby sequence of the images of portions of the lens 200 is generated. The sequence of images can include, for instance, nine images and can be merged to get a total image of the entire lens 200 or substantially the entire lens 200 as a result. Consequently, the Magnified FOV station 106 can have a resolution as small as 2.5 μm in size.

Figure 3:
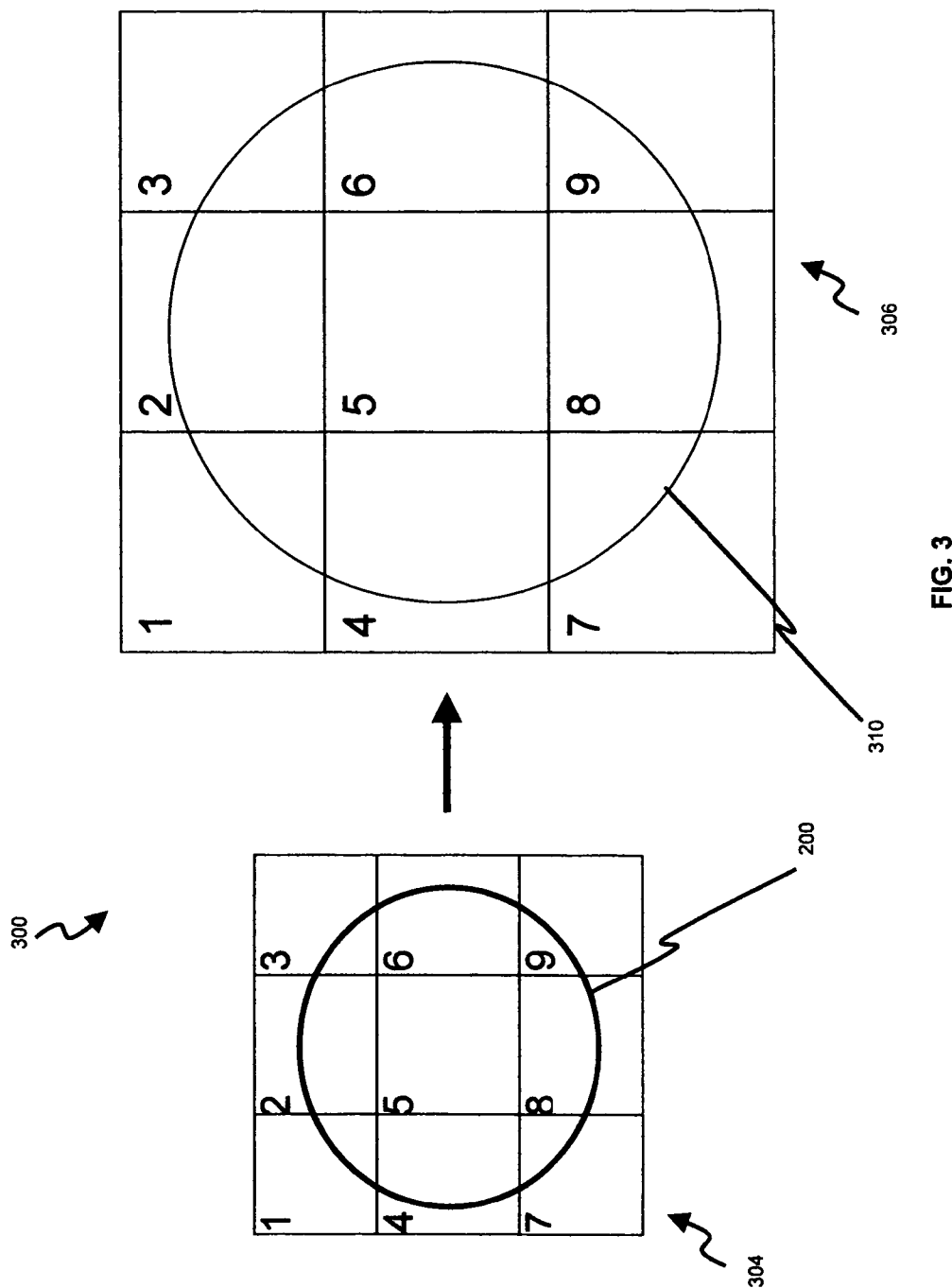
FIG. 3 shows an FOV image of an object that can be split into nine portions (as shown on left side of the figure) and nine corresponding magnified images captured by the Magnified FOV station. The nine magnified images can be merged to obtain a total whole image of the object (as shown on right side of the figure)

The nine aforementioned portions of the object 200 are shown in FIG. 3. The object 200 is placed under the full FOV station to obtain image portions 304. The magnified FOV station 106 can generate nine proper images that can be merged to get magnified image portions 306 and the magnified image 310 of the whole object 200.

Although the magnified image 306 is shown in FIG. 3 as being partitioned into nine segments, the magnified image 306 can be partitioned into any number of segments depending on the specifications of the defects to be inspected.

Figure 4:
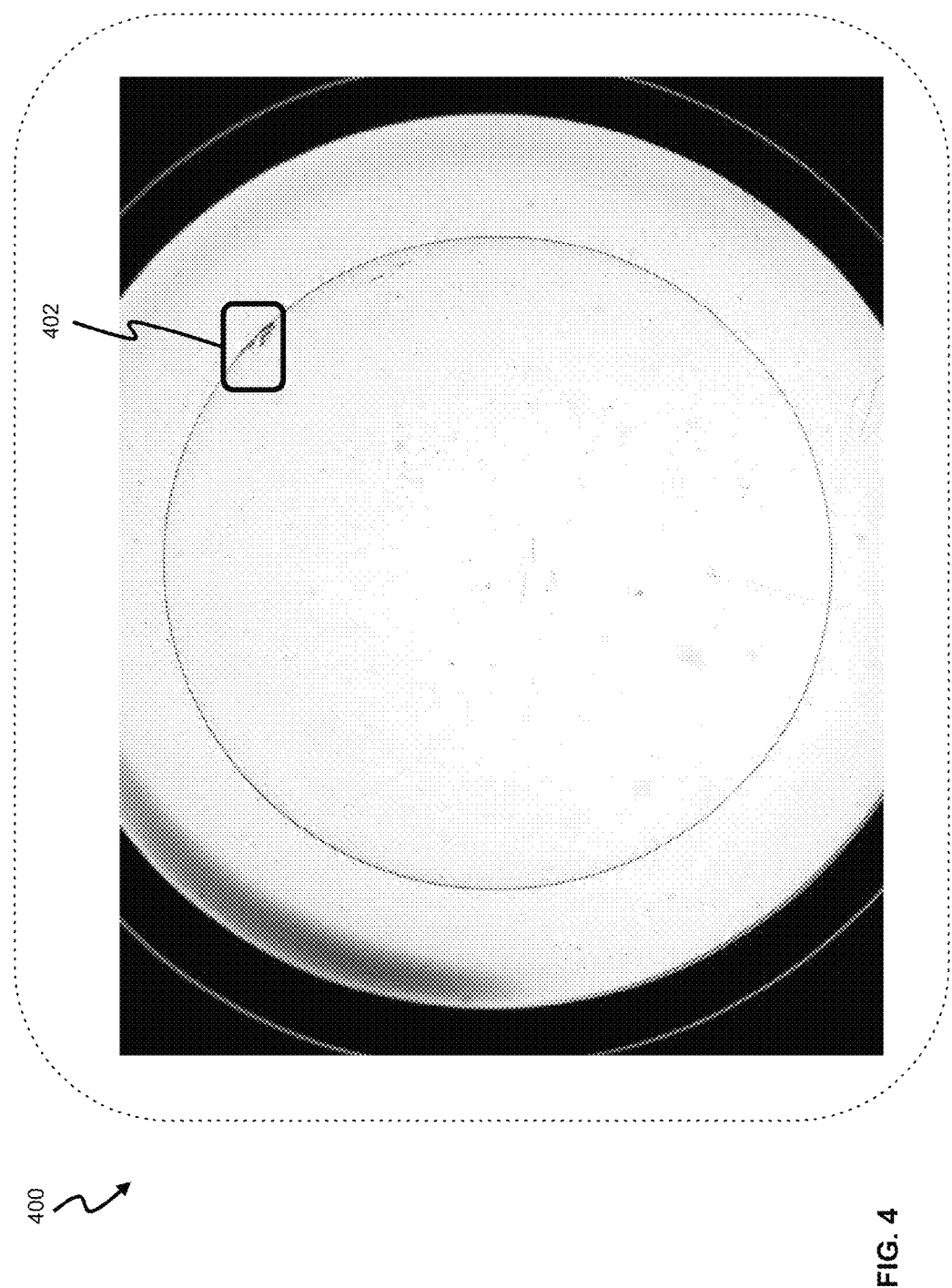
FIG. 4 shows an image of a lens captured by the Full FOV station of FIG. 2.
Figure 5:
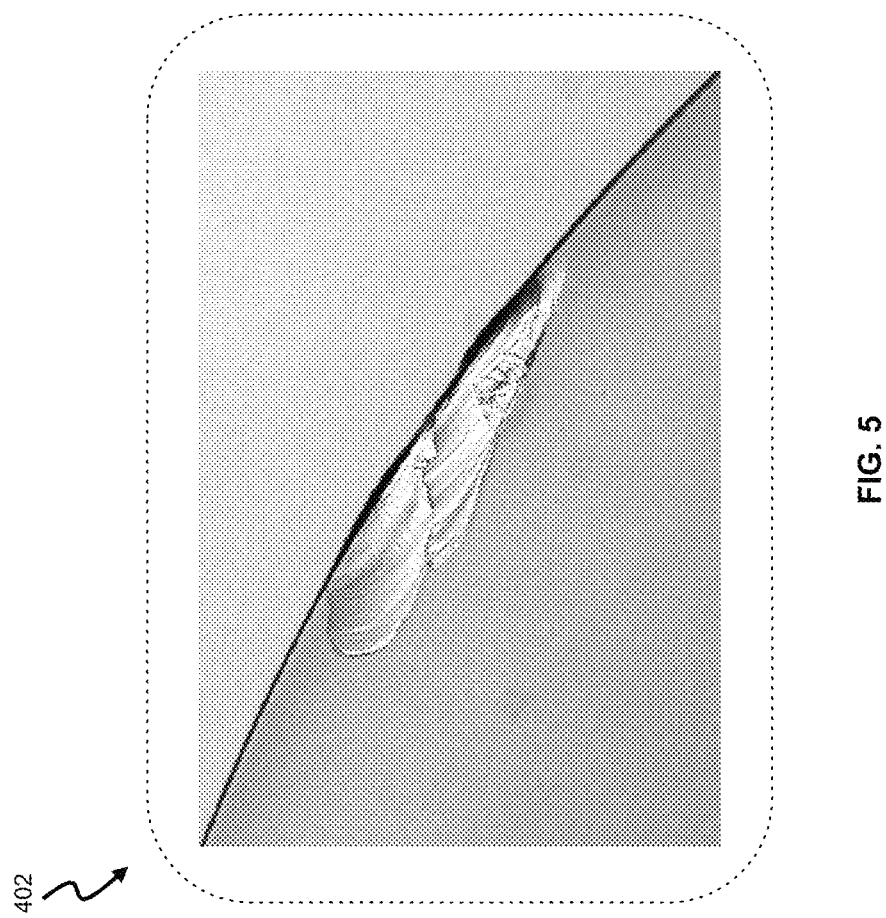
FIG. 5 shows an image of a portion of the lens captured by the Magnified FOV station of FIG. 2 in which the portion of the lens containing the defects is identified from the image of FIG. 4.

FIG. 4 shows an image 400 of a sample lens captured by the Full FOV station 104 whereas FIG. 5 shows an image 402 of a portion of the sample object (e.g., lens) magnified by the Magnified FOV station 106. Defects present on the portion of the sample lens were identified after digitally processing and evaluating the image 400 and image 402 to determine whether the defects are acceptable or unacceptable.

Figure 6:
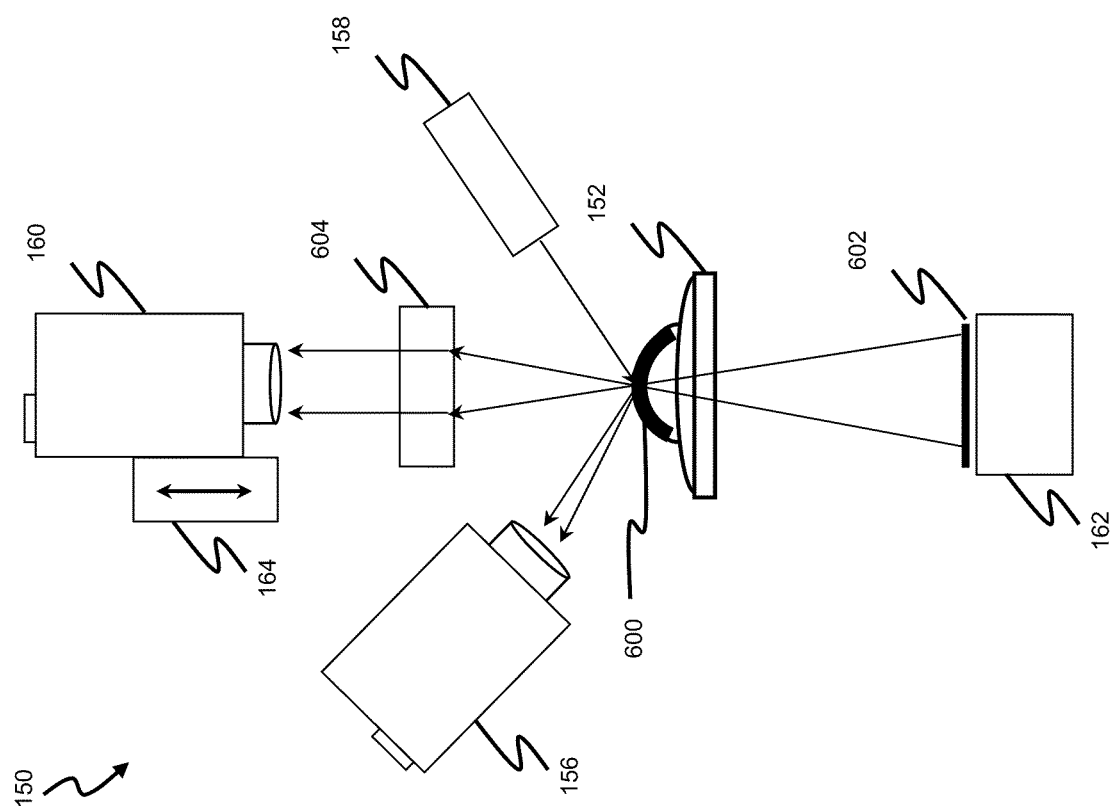
FIG. 6 shows a lens characteristic measurement subsystem of the high-resolution lens inspection system of FIG. 1 in which the lens characteristic measurement subsystem comprises a lens power meter station and a lens thickness meter station.

FIG. 6 shows the lens characteristic determination subsystem 150, which comprises two stations for measuring the lens power and lens thickness. A first station for measuring the lens power comprises the fourth detection means 160 and the fourth illumination means 162, motor 164, the imaging lens 604 and the test target 602. The imaging lens 604 in combination with a lens 600 generates an image of the test target 602. The image is captured by detection means 160 that is movable by motor 164 along the optical axis of the imaging lens 604. Hence, the detection means 160 adjusts the image of the test target 602 by adjusting the position of the detection means 160 by motor 164. The lens power of a lens 600 is measured by providing a test image 602 to thereby enable the fourth detection means 160, together with the usage of an imaging lens 604, to capture a virtual image (not shown) of the test image 602. Equations for determining the lens powers and magnification ratio of a lens are expressed as:

$$\frac{1}{u} + \frac{1}{v} = \frac{1}{f} \quad (1a)$$

$$M = \frac{u}{v} \quad (1b)$$

in which u is the distance of the virtual image from the lens, v is the distance of the object from the lens, f is the focal length of the lens and M is the magnification ratio of the lens.

Equations (1a) and (1b) are known as the Thin Lens formula and the Magnification formula respectively, as well known to practitioners in the art. Hence, by adjusting the position of the fourth detection means 160 until a virtual image of the test image 602 is captured by the fourth detection means 160, both the focal length and the magnification ratio of the lens 600 are then computable using equations (1a) and (1b). By definition, the lens power, P, is given as P=1/f.

A second station for determining the lens thickness comprises the third detection means 156 and the third illumination source 158. The third illumination source 158 emits beams which are directed at an angle towards the center of the lens 600. The beams are preferably one of laser beams and light beams. Subsequently, the beams reflected by the lens 600 are received by the third detection means 156 and further processed for obtaining a set of optical information, by which a lens thickness can be determined based upon techniques known to practitioners in the art.

Figure 7:
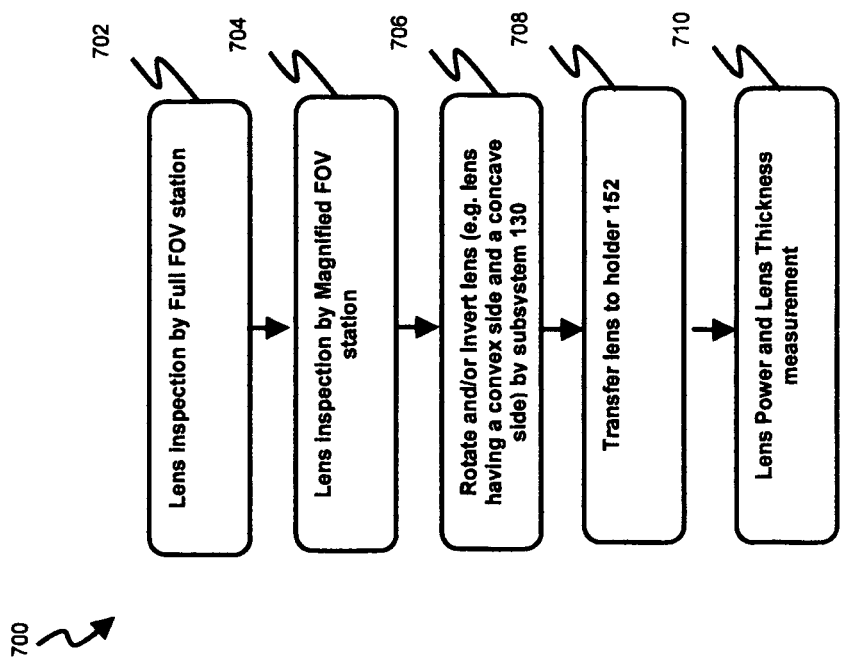
FIG. 7 shows a flowchart illustrating a lens inspection process performed by the high-resolution lens inspection system of FIG. 1.

FIG. 7 shows a flowchart illustrating a lens inspection process 700 performed by the high-resolution object inspection system 100. Firstly in step 702, the Full FOV station 104 captures an image of a lens under inspection. The image is then digitally processed and evaluated to detect defects on the lens. If defects are detected, the lens is then transferred to the Magnified FOV station 106. Optionally, even if no defects are detected by the Full FOV station 104, the lens is still transferred to the Magnified FOV station 106 for further inspection to detect defects that are not detectable by the Full FOV station 104.

At the Magnified FOV station 106, magnified images of portions of the lens containing the defects are captured in step 704. The magnified images are then further inspected to determine whether the lens can be accepted. The lens is then transferred to the subsystem 130. The lens can then be rotated and/or inverted by subsystem 130 in step 706. The subsystem 130 picks up the lens and put it on the lens holder 152 in step 708. The lens holder 152 can then be transferred to the lens characteristic determination subsystem 150. The lens characteristic subsystem 150 measures the lens power and lens thickness in step 710.

In the foregoing manner, a high-resolution inspection system for performing object inspection is described according to various embodiments of the invention for addressing the foregoing disadvantages of conventional lens inspection systems. Although a few embodiments of the invention are disclosed, it will be apparent to one skilled in the art in view of this disclosure that numerous changes and/or modifications can be made without departing from the scope and spirit of the invention.

The invention claimed is:

1. An lens inspection system for inspecting a lens for presence or absence of lens defects, the lens having an optical axis, the system comprising:
   a first station configured to capture a first image of the lens in which the lens is provided in a first orientation, the first image being processable to determine one of presence and absence of at least one defect on the lens;

a second station configured to capture at least one second image of the lens, the at least one second image being a magnified view of at least one portion of the lens, the at least one second image being processable to determine quality of the at least one defect on the lens, the quality of the at least one defect on the lens being one of acceptable and unacceptable; and a third station configured to determine at least one optical property of the lens upon an absence of the at least one defect on the lens, or in the presence of the at least one defect on the lens in the event that the quality of the at least one defect on the lens is acceptable, wherein the third station comprises:

a backlighting illuminator disposed on a first side of the lens, the backlighting illuminator configured to direct illumination toward the lens and through a test image that is separate from the lens; and a camera disposed on a second side of the lens opposite to the first side of the lens, the camera configured to detect an image corresponding to illumination output by the backlighting illuminator and directed through each of the test image and the lens.

2. The lens inspection system as in claim 1, wherein the first station comprises:

a light source for illuminating the lens; and
an image capture means for capturing the first image of the lens illuminated by the light source.

3. The lens inspection system as in claim 2, wherein the image capture means includes one of a complementary metal-oxide semiconductor (CMOS) sensor and a charge-coupled device (CCD).

4. The lens inspection system as in claim 2, wherein the light source is positioned to emit light along an optical path that includes the lens and the image capture means.

5. The lens inspection system as in claim 1, wherein the second station comprises:

a light source for illuminating the lens;
an image capture means for capturing the at least one second image of the lens illuminated by the light source; and
an optical scanner being operable for magnifying view of the at least one portion of the lens and for directing the magnified view of the at least one portion of the lens towards the image capture means.

6. The lens inspection system as in claim 5, wherein the optical scanner is a mirror galvanometer.

7. The lens inspection system as in claim 5, wherein the image capture means of the second station includes one of a complementary metal-oxide semiconductor (CMOS) sensor and a charge-coupled device (CCD).

8. The lens inspection system as in claim 5, wherein the optical scanner includes one of a positionable mirror and a steerable mirror.

9. The lens inspection system as in claim 5, wherein the light source of the second station is positioned to emit light along an optical path that includes the lens and the image capture means of the second station.

10. The lens inspection system as in claim 1, wherein the optical property of the lens being determined is at least one of the thickness of the lens and the focal length of the lens.

11. The lens inspection system as in claim 1, further comprising a subsystem configured to move the lens between stations.

12. The lens inspection system as in claim 11, wherein the subsystem is configured to rotate the lens by 180°.

13. The lens inspection system as in claim 11, wherein the subsystem is configured to invert the lens in association with an inspection process.

14. The lens inspection system of claim 1, wherein the camera and the lens are displaceable relative to each other along a plane parallel to the optical axis of the lens.

15. The lens inspection system of claim 1, wherein the first image and/or the at least one second image is processable to determine whether an aberration defect is present on the lens.

16. An lens inspection method for inspecting a lens for presence of absence of lens defects, the lens having an optical axis, the method comprising:

capturing a first image of the lens by a first station, the lens being provided in a first orientation and the first image being processable to determine one of presence and absence of at least one defect on the lens;

capturing at least one second image of the lens by a second station, the at least one second image being a magnified view of at least one portion of the lens, the at least one second image being processable to determine quality of the at least one defect on the lens, the quality of the at least one defect on the lens being one of acceptable and unacceptable; and determining at least one optical property of the lens by a third station upon an absence of the at least one defect on the lens or in the presence of the at least one defect on the lens in the event that the quality of the at least one defect is acceptable, wherein determining the at least one optical property of the lens comprises:

directing backlight illumination from a first side of the lens toward the lens and through a test image that is separate from the lens; and detecting an image corresponding to backlight illumination directed through each of the test image and the lens using a camera disposed on a second side of the lens opposite to the first side of the lens.

17. The lens inspection method as in claim 16, wherein capturing a first image of the lens by the first station comprises:

providing a light source for illuminating the lens; and
capturing the first image of the lens illuminated by the light source by an image capture means.

18. The lens inspection method as in claim 17, wherein capturing a first image of the lens by the first station comprises:

providing a laser beam emitting source for illuminating the lens; and
capturing the first image of the lens illuminated by the laser beam emitting source using one of a complementary metal-oxide semiconductor (CMOS) sensor and a charge-coupled device (CCD).

19. The lens inspection method as in claim 17, further comprising positioning the light source to emit light along an optical path that includes the lens and the image capture means.

20. The lens inspection method as in claim 16, wherein capturing at least one second image of the lens by the second station comprises:

providing a light source for illuminating the lens;
capturing the at least one second image of the lens illuminated by the light source by an image capture means; and
magnifying view of the at least one portion of the lens and directing the magnified view of the at least one portion of the lens towards the image capture means by an optical scanner.

21. The lens inspection method as in claim 20, wherein capturing at least one second image of the lens by the second station comprises magnifying view of the at least one portion of the lens and directing the magnified view of the at least one portion of the lens towards the image capture means by a mirror galvanometer.

22. The lens inspection method as in claim 20, wherein capturing at least one second image of the lens by the second station comprises:
   providing a laser beam emitting source for illuminating the lens; and
   capturing the at least one second image of the lens illuminated by the laser beam emitting source using one of a complementary metal-oxide semiconductor (CMOS) sensor and a charge-coupled device (CCD).

23. The lens inspection method as in claim 20, further comprising positioning the light source of the second station to emit light along an optical path that includes the lens and the image capture means of the second station.

24. The lens inspection method as in claim 16, wherein determining the optical property of the lens comprises determining at least one of the thickness of the lens and the focal length of the lens.

25. The lens inspection method of claim 16, wherein the camera and the lens are displaceable relative to each other along a plane parallel to the optical axis of the lens.

26. The lens inspection method of claim 16, further comprising processing the first image and/or the at least one second image to determine whether an aberration defect is present on the lens.

* * * * *